US006042830A

United States Patent [19]
Chladek et al.

[11] Patent Number: 6,042,830
[45] Date of Patent: *Mar. 28, 2000

[54] VIRAL AGENT ASSOCIATED WITH MYSTERY SWINE DISEASE

[75] Inventors: Danny W. Chladek; David E. Gorcyca, both of St. Joseph; Louis L. Harris, Forsythe, all of Mo.

[73] Assignee: Boehringer Ingelheim Vetmedica, Inc., St. Joseph, Mo.

[*] Notice: This patent is subject to a terminal disclaimer.

[21] Appl. No.: 08/440,750

[22] Filed: May 15, 1995

Related U.S. Application Data

[63] Continuation-in-part of application No. 08/207,563, Mar. 7, 1994, Pat. No. 5,476,778, which is a continuation of application No. 08/071,118, Jun. 1, 1993, abandoned, which is a continuation of application No. 07/921,891, Aug. 5, 1992, abandoned.

[51] Int. Cl.[7] .......................... A61K 39/00; A61K 39/38; C12N 7/08
[52] U.S. Cl. .................................. 424/184.1; 424/218.1; 424/221.1; 424/204.1; 424/815; 435/235.1; 435/236; 435/237; 435/239
[58] Field of Search .................... 435/237, 236, 435/239, 235.1, 5, 173.3; 424/204.1, 218.1, 221.1, 815

[56] References Cited

U.S. PATENT DOCUMENTS

| | | |
|---|---|---|
| 5,476,778 | 12/1995 | Chladek et al. . |
| 5,510,258 | 4/1996 | Sanderson et al. . |

FOREIGN PATENT DOCUMENTS

| | | |
|---|---|---|
| 0595436 | 4/1994 | European Pat. Off. . |
| 2282811 | 4/1995 | United Kingdom . |
| 9303760 | 4/1993 | WIPO . |

OTHER PUBLICATIONS

Conzelmann et al., *Virology*, "Molecular Characterization of Porcine Reproductive and Respiratory Syndrome Virus, a Member of the Arterivirus Group," vol. 193, p. 329–339, 1993.
Benfield, David A. et al., *J. Vet. Diagn Invest*, "Characterization of sine infertility and respiratory syndrome (SIRS) virus (isolate ATCC VR–2332)," vol. 4, p. 127–133, 1992.
Goyal, Sagar M., *J. Vet. Diagn Invest*, "Porcine reproductive and respiratory syndrome," vol. 5, p. 656–664, 1993.
Meulenberg, Janneke J.M., *Virology*, "Lelystad Virus, the Causative Agent of Porcine Epidemic Abortion and Respiratory Syndrome (PEARS), is Related to LDV and EAV," v. 192, p. 62–72, 1993.
Murtaugh, Micheal, *The Evolution of the Swine Veterinary Profession*, "The PRRS Virus," vol. 20, p. 43–45, 1993.
Dacso, C.C. et al., 1984, "Sporadic Occurrence of Zoonotic Swine Influenze Virus Infections", J. Clin. Microbiology 20(4):833–835.

Derbyshire, J.B., 1958, "Porcine Enterovirus Infections", *Diseases of Swine,* Fifth Edition, Chapter 20 pp. 265–271.
Goldfield, M. et al., 1977, "Influenza in New Jersey in 1976: Isolations of Influenza A/New Jersey/Virus at Fort Dix", J. of Infectious Disease 136 Supp.:S347–S355.
Goldstein, M.A. et al., 1970, "Evaluation of Three Cell Culture Systems as Substrates for Influenza Virus Assay", Applied Microbiology 19(4):580–582.
Graves, J.H., 1958, "Swine Vesicular Disease", *Diseases of Swine,* Fifth Edition, Chapter 23 pp. 288–293.
Gustafson, D.P., 1958, "Pseudorabies", *Disease of Swine,* Fifth Edition, Chapter 14 pp. 209–223.
Heath, R.B. & Tyrrell, 1958, "The Behavior of Some Influenza Viruses in Tissue Cultures of Kidney Cells of Various Species", Archiv. F. Virusorschung B.d VIII, HS. pp. 577–591.
Hofman, M. & Wyler, R., 1988, "Propagation of the Virus of Porcine Epidemic Diarrhea in Cell Culture", J. Clin. Microbiol. 26(11):2235–2239.
McDaniel, H.A., 1958, "African Swine Fever", *Diseases of Swine,* Fifth Edition, Chapter 16 pp. 237–245.
McFerran, J.B., 1958, "Reovirus Infection", *Diseases of Swine,* Fifthe Edition, Chapter 28 pp. 330–334.
McQueen, J.L. et al., 1968, "Influenza in Animals", Advances in Veterinary Science 12:285–337.
Pan, I.C. et al., 1980, "Replication of African Swine Fever Virus in Cell Cultures", Am. J. Vet. Res. 41(9):1357–1367.
Patriarca, P.A. et al., 1984, "Lack of Significant Person–to–Person Spread of Swine Influenza–Like virus Following Fatal Infection in an Immunocompromised Child", Am. J. Epidemiology 119(2):152–158.
Smith, T.F. et al., 1976, "Isolation of Swine Influenza Virus From Autopsy Lung Tissue of Man", New Engl. J. Med. 708–710.
Stim, T.B., 1969, "Arbovirus Plaquing in Two Simian Cell Lines", J. Gen. Virol. 5:329–338.
Travassos da Rose, A.P. et al., 1984, "Carajas and Maraba Viruses, Two New Vesiculoviruses Isolated From Phlebotomine Sand Flies in Brazil", Am. J. Trop. Med. Hyg. 33(5):999–1006.
Woode, G.N. & Bohl, E.H., 1958, "Porcine Rotavirus Infection", *Disease of Swine,* Fifth Edition, Chapter 26 pp. 310–322.
Levy et al.; Freeze–Drying is an Effective Method for Preserving Infectious Type C Retroviruses; *J. Virol. Methods,* 5 (1982) 165–171.

(List continued on next page.)

*Primary Examiner*—Lynette R. F. Smith
*Assistant Examiner*—Datquan Lee
*Attorney, Agent, or Firm*—Robert Raymond; Mary-Ellen M. Devlin; Alan Stempel

[57] ABSTRACT

A substantially avirulent vaccine against Porcine Reproductive and Respiratory Syndrome (PRRS) is provided, which effectively immunizes swine against the U.S. and European forms of the disease, together with a method of growing the viral agent in vitro, and a method of attenuating the virus for vaccine preparation.

16 Claims, 1 Drawing Sheet

OTHER PUBLICATIONS

Stevenson et al.; Endemic porcine reproductive and respiratory syndrome virus infection of nursery pigs in twoswine herds without current reproductive failure; *J. Vet Diagn. Invest.* 5:432–434 (1993).

Murphy et al.; Immunization Against Viruses; Chapter 19; *Virology*; 2d Ed., Raven Press Ltd., New York 1990.

Beare et al., "Further Studies in Man of Hsw1N1 Influenza Viruses," *Journal of Medical Virology*, 5:33–38 (1980).

Berendt et al., "Reaction of Squireel Monkeys to Intratracheal Inoculation with Influenza/A/New Jersey/76 (Swine) Virus," *Infection and Immunity*, pp. 476–479 (1977).

Berendt et al., "Evaluation of Commercially Prepared Vaccines for Experimentally InducedType/A/New Jersey/8/76 influenza Viruse Infections in Mice and Squirrel Monkeys," *The Jouranl fo Infectious Disease*, vol. 136, pp. S712–S718, Supplement (1977).

Bohl et al., "Isolation and Serotyping of Porcine Rotaviruses and Antigenic Comparison with Other Rotaviruses," *Journal of Clinical Microbiology*, pp. 105–111, (1984).

Bouillant et al., "Viral Susceptibility of a Cell Line Derived from the Pig Oviduct," *Can. J. cop. Med.*, vol. 39, pp. 450–456, (1975).

Cabasso et al., "Propagation of Infectious Canine Hepatitis Virus in Tissue Culture, (20843)," *P.S.E.B.M.*, v85, pp. 239–245, (1954).

Callebaut et al., "Antigentic Differentiation between Transmissible Gastroenteritis virus of Swine and a Related Porcine Respiratory Coronavirus," *J. gen. Virol.*, 69, 1725–1730, (1988).

Charley, "Interaction of Influenza Virus With Swine Alveolar Macrophages: Influence of anti–virus Antibodies and Cytochalasin B," *Ann. Virol. (Inst. Pasteur)*, 134 E, 51–59, (1983).

Dea et al, "Antigenic Variant of Swine influenza Virus Causing Proliferative and Necrotizing Pneumonia in Pigs," *J. vet. Diagn. Invest.*, vol. No. 4, pp. 380–392 (Apr. 1992).

Dea et al., "Caractéristiques d'isolats des virus influenza et de l'enc´´ohalomyocardite associés au Syndrome Reproducteur et Respiratoire Porcin (S.R.R.P.) au Québec," *Le Médecin Vétérinaire De Québec*, vol. 21, No. 4, pp. 170–175, (Nov. 1991). A copy of an English translation is attached.

Easterday, "Swine Influenza," *Diseases of Swine*, 6th Edition, pp. 244–255, (1986).

Girard, et al, "Experimentally Induced Porcine Proliferative and Necrostising Pneumonia with an Influenza A Virus," *The Veterinary Record*, (1992) 130, 206–207, Mar. 7, 1992.

gourreau et al., "Diffusion Du Virus De La Grippe Du Porc (H1N1 =Hsw1N1) En France," *Ann. Virol. (Inst. Pasteur)*, 132 E, 287–294 (1981).

Grizzard et al, "Experimentally Production of Respiratory Tract Disease in Cebus Monkeys After Intratracheal or Intranasal Infection with Influenza A/Victoria/3/75 or Influenza A/New Jersey/76 Virus," *Infection and Immunity*, vol. 21, No. 1, pp. 201–205, (1978).

Imagawa et al., "Isolation of Foal Rotavirus in MA–104 Cells," *Bull. Equine Res. Inst.*, No. 18, 119–128 (1981).

Johnson, "Feline Panleucopaenia Virus: IV.—Methods for Obtaining Reproducible in vitro Results," *Res. vet. Sci.*, 8, pp. 256–265, (1967).

Kundin, "Hong Kong A–2 Influenza Virus Infection among Swine during a human Epidemic in Taiwan," *Nature*, vol. 228, p. 857 and cover page.

Madec et al., "Consequences Pathologiques D'un Episode Grippal Severe (Virus Swine A/$H_1N_1$) Dans Les Conditions Naturelles Chez La Truie Non Immune En Debut De Gestation," *Comp. Immun. Microbiol. Infect. Dis.*, vol. 12, No. 1/2, pp. 17–27, (1989).

Meikeljohn et al., "Respiratory Virus Vaccine Evaluation and Surveillance," *Semi–Annual Contract Progress report to the National Institute of Allergy and Infectious Diseases*, 21 ogs., (Sep. 15, 1965 to Mar. 15, 1966).

Morin et al., "Severe proliferative and necrotizing pneumonia in pigs: A newly recognized disease," *Can Vet J*, vol. 31, pp. 837–839 (Dec. 1990).

Moore et al., "Porcine Proliferative and Necrotyzing Pneumonia Clinical Findings," *Presented at American Association of Swine Practitioners. 22nd Annual Meeting*, pp. 443–453 (Mar. 3–5, 1991.

Moore, C., "Porcine Proliferative and Necrotyzing Pneumonia Clinical Findings," *Presented at American Assoication of Swine Practitioners, 2nd Annual Meeting*, pp. 443–453 (Mar. 3–5, 1991).

Murakami et al., "Difference in growth behavior of human, swine, equine, and avian influenza viruses at a high temperature," *Arch Virol*, 100:231–244 (1988).

Nakamura et al., "Studies on Swine Influenza. III. Propagation of Swine Influenza Virus in Explants of Respiratory Tract Tissues from Fetal Pigs," *Studies on Swine Influenza*, pp. 27–35, (1968).

Pirtle et al., "Morphologic Heterogeneity of a Strain of Swine Influenza Virus (A/Swine/Wisconsin/1/68, Hsw1N1) Propagated at Different Temperatures," *Am J Vet Res*, vol. 36, No. 1, pp. 1783–1787 (1975).

Polson et al., "Financial Implications of Mystery Swine Disease (MSD)," Livestock Conservation Institute Proceedings, *Mystery Swine Disease Committee Meeting*, pp. 8–27, Oct. 6, 1990.

Potgieter et al, "Isolation of Swine Influenza Virus in Oklahoma," *JAVMA*, vol. 171, No. 8, pp. 758–760, (1977).

Reed et al., "Persistent Respiratory Virus Infection in tracheal Organ Cultures," *Br. J. exp. Path.*, 50, 378–388, (1969).

Schmidt et al., "Infection by Influenza A Viruses of Tracheal Organ Cultures Derived from Homologous and Heterologous Hosts," *The Journal of Infectious Diseases*, vol. 129, No. 1, pp. 28–36, (1974).

Stephen et al., "Swine Influenzae Virus Vaccine: Potentiation of Anitbody Responses in Rhesis Monkeys," pp. 1289–1290, (1977).

Stephen et al., "Swine Influenza Virus Vaccine: Potentiation in Rhesus Monkeys in Antibody Responses by a Nuclease Resistant Derivatives of Poly I–Poly C," U.S. Army Medical Research Institute of Infectious Diseases, Fort Detrick, Frederick, MD 21701, 12 pages (double–sided), (1976).

Theil et al., "Isolation and Serial Propagation of Turkey Rotaviruses in a Fetal Rhesus Monkey Kidney (MA104) Cell Line," *Avian Diseases*, vol. 30, No. 1, pp. 93–104 (1985).

Tobita et al., "Plaque Assay and Primary Isolation of Influenza A Viruses in an Established Line of Canine Kidney Cells (MDCK) in the Presence of Trypsin," *Med. Microbiol. Immunol.*, 162, 9–14 (1975).

Urasawa et al., "Sequential Passages of Human Rotavirus in MA–104 Cells," *Microbiol. Immunol.*, vol. 25 (10), 1025–1035, (1981).

van Nieuwstadt et al, "Infection with porcine respiratory coronavirus does not fully protect pigs against intestinal transmissible gastroeneteritis virus," *The Veterinary Record,* pp. 58–60, (1989).

Webster et al., "Chemotherapy and Vaccination: a Possible Strategy for the Control of Highly Virulent Influenza Virus," *Journal of Virology,* vol. 55, No. 1, pp. 173–176, (1985).

Woods et al., "Antigenicity of Inactivated Swine Influenza virus Concentrated by Centrifugation," *Research Communications in Chemical Pathology and Pharmacology,* vol. 13, No. 1, pp. 129–132, (1976).

Woods et al., "Experimental Challenge of Pregnant Gilts with swine Influenza virus After Vaccination," *Research Communications in Chemical Pathology and Pharmacology,* vol. 15, No. 4, pp. 787–795, (1976).

Woods et al., "Investigation of Four Outbreaks of Acute Respiratory Disease in Swine and Isolation of Swine Influenza Virus," *Swine Influenza,* vol. 5, No. 4, H.L.S., pp. 218–224, (1968).

Yamane et al., "Annual Examination of Influenza Virus Infection among Pigs in Miyagi Prefecture, Japan: The Appearance of Hsw1N1 Virus," *Acta. virol.,* 23: 240–248 (1979).

Christianson, et al.; Experimental reproduction of swine infertility and respiratorysyndrome in pregnant sows; Am. J. Vet Res., vol. 53, No. 4, Apr., 1992, pp. 485–488.

Collins et al.; Isolation of swine infertility and respiratory syndrome virus (isolate ATCC VR–2332) in North American and experimental reproduction of the disease in gnotobiotic pigs; J. Vet Diagn. Invest; 4:117–126 (1992).

Wensvoort et al.; Antigenic comparison of Lelystad virus and swine infertility ans respirary syndrome (SIRS) virus; J. Vet Diagn. Invest. 4:134–138 (1992).

Yoom et al.; Isolation of a cytopathic virus from weak pigs on farms with a history of swine infertility and rspiratory syndrome; J. Vet Diagn. Invest. 4:139–143 (1992).

Morrison et al.; Serologic evidence incriminating a recently isolated virus (ATCC VR–2332) as the cause of swine infertility and respiratory syndrome (SIRS); J. Vet. Diagn. Invest. 4:186–188 (1992).

Halbur et al.; Viral pneumonia in neonatal and nursery pigs. Agri–Practice; Jan./Feb. 1991, vol. 12, No. 1.

Wensvoort et al.; Mystern swine disease in the Neterhalnds: the isolation of Lelystad virus; The Veterinary Quarterly, vol. 13, No. 3, Jul. 1991.

Terpstra et al.; Experimental reproduction of porcine epidemic abortion and respiratory syndrome (mystery swine disease) by infection with Lelystad virus; Koch's postulates fulfilled; The Veterinary Quarterly, vol. 13, No. 3, Jul. 1991.

Pol et al.; Pathological, ultrastrutural and immunohistochemical changes caused bu Lelystad virus in experimentalliy induced infections of mystery swine disease; The Veterinary Quarterly, vol. 13, No. 3, Jul. 1991.

Polson et al.; Financial implications of Mystern Swine Disease: Livestock Conservation Institute, Proceedings, Mystery Swine Disease Committee Meeting, Oct. 6, 1990; Denver, CO.

Weensvoort, Letters, The Veterinary Records, Jun. 15, 1991, p. 574.

AASP Newsletter, vol. 1, No. 2, Sep.–Oct. 1989.

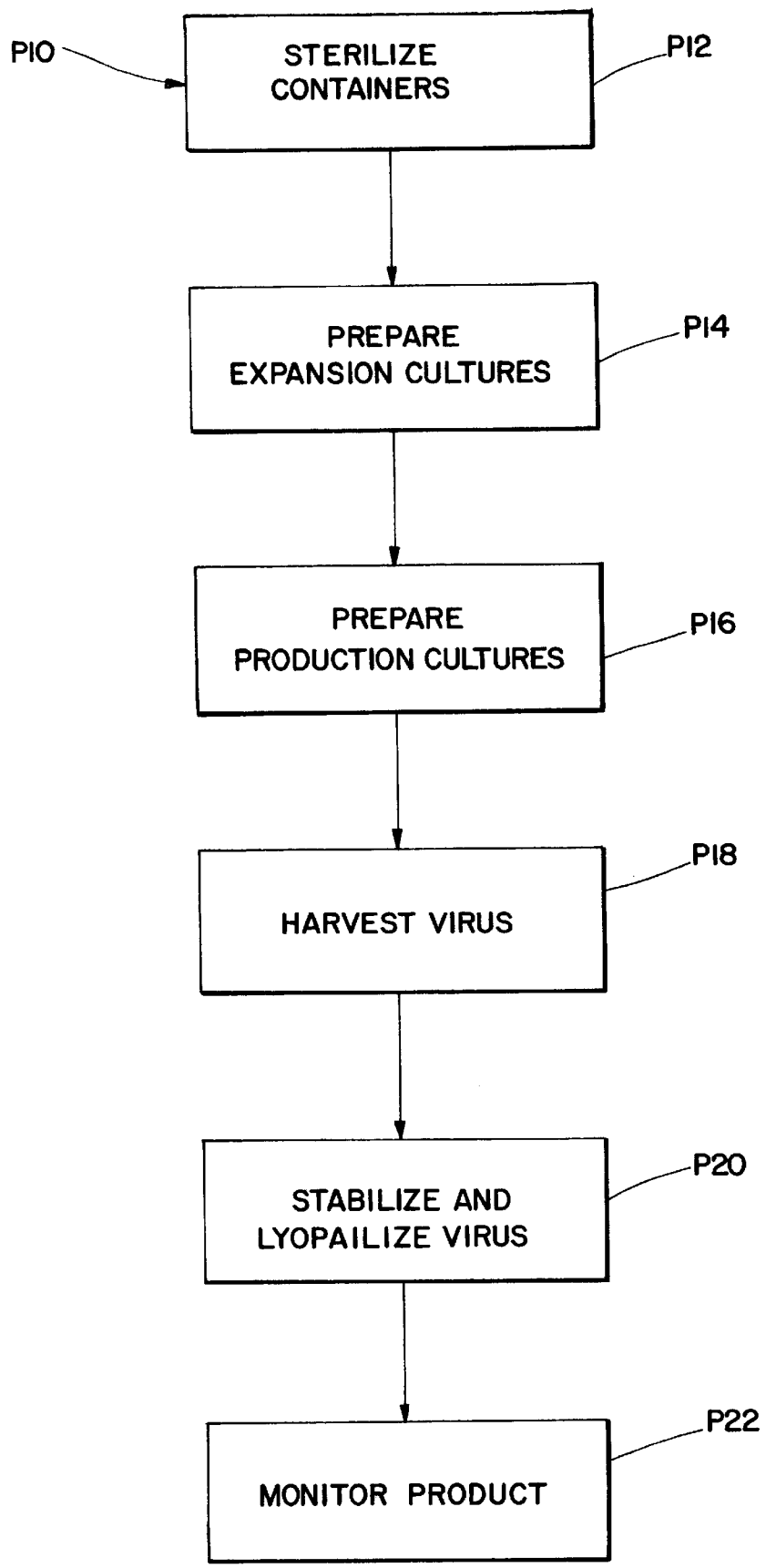

VIRAL AGENT ASSOCIATED WITH MYSTERY SWINE DISEASE

RELATED APPLICATION

This application is a continuation-in-part of application Ser. No. 08/207,563, filed Mar. 7, 1994 now U.S. Pat. No. 5,476,778, which application was a continuation of application Ser. No. 08/071,118, filed Jun. 1, 1993, which was a continuation of application Ser. No. 07/921,891, filed Aug. 5, 1992. Applications Ser. Nos. 07/921,891 and 08/071,118 are now abandoned.

BACKGROUND OF THE INVENTION

1. Field of the Invention

The present invention pertains to the field of immunology and virology and, more particularly, to a vaccine derived from a pathogenic viral isolate. More specifically, the pathogenic form of the virus is modified or attenuated to an avirulent form according to methods of producing the vaccine for use against a devastating new swine disease.

2. Description of the Prior Art

A new swine disease, variously referred to as "mystery swine disease", "swine infertility and respiratory syndrome", "blue ear disease", or "porcine reproductive and respiratory syndrome" (PRRS) is causing heavy losses in breeding herds of the United States and Canada. A similar disease has also appeared in much of Europe. The disease is manifested in two forms, one causing reproductive failure and the other producing respiratory distress in young pigs. The reproductive form of the disease is described by Keffaber, K. K., "Reproductive Failure of Unknown Etiology", American Association of Swine Practitioners Newsletter, 1:109 (1989).

The most prominent clinical symptoms of the reproductive form of the disease are spontaneous late-term abortions, premature births (which can be as high as 20–30% of all births) and the farrowing of mummified fetuses, stillbirth or sickly piglets. Such clinical symptoms will typically be observed in a herd from 4–16 weeks, or even longer. Stillborn fetuses in affected litters often are in the early stages of mummification, as evidenced by tan-brown discoloration of the skin and post-mortem autolysis. Dome-shaped malformations of fetal skulls is also sometimes seen. The infection of sows may go unnoticed, or may manifest itself by an impaired general condition lasting up to a few days. For example, the sows may go off feed, and experience body temperatures either above or below normal. In the farrowing phase, the sows may exhibit depression, lethargy, phyrexia and occasional vomiting. In some affected herds, up to 75% of all piglets may be lost. The economic consequences of the disease, accordingly, are devastating.

The respiratory form of the disease exhibits clinical signs which are most pronounced in piglets of 3–8 weeks in age, but are reported to occur in pigs of all ages in infected herds. The diseased piglets grow slowly, have roughened hair coats, respiratory distress ("thumping") and increased mortality (up to about 80% pre-weaning mortality).

Findings in preliminary studies of gross and microscopic lesions of piglets affected with the respiratory form of the disease suggest that microscopic lung lesions are an important clinical feature of this disease. Despite pronounced respiratory symptoms of disease, lungs that appear uncomplicated by secondary bacterial infection are either grossly normal or have a mild, diffused tan-gray discoloration of the lung surface. Nevertheless, a microscopic examination of the lung tissue of PRRS-diseased piglets reveals a characteristic pattern of interstitial pneumonitis, per Collins, J. E. et al., "Respiratory Disease in a Swine Herd Experiencing a Reproductive Failure Syndrome", Proceedings, Minnesota Swine Conference for Veterinarians, p. 254, St. Paul, Minn. (Sep. 10–18, 1990).

Accordingly, there is a real need in the art for an effective vaccine which can eliminate or at least ameliorate the effects of PRRS.

SUMMARY OF THE INVENTION

The present invention overcomes the problems outlined above by providing a vaccine that effectively reduces or prevents the disease caused by PRRS virus in swine.

Broadly speaking, the invention includes a biologically or virally pure culture of PRRS virus together with all mutants thereof and methods of producing and using these virions. The wild-type virus is capable of causing PRRS in swine, but modified forms of the virus, or non-pathogenic mutants thereof, provide an effective vaccine against this disease. The vaccine preferably includes a live modified or attenuated virus and a pharmaceutically effective carrier agent. The modified virus is preferably propagated and maintained in a simian kidney cell line, and this cell line is most preferably MA-104 which is African Green Monkey Kidney cells passed twenty or more times.

A pathogenic viral agent was recovered from the tissue homogenate of an infected pig, and confirmed by causing PRRS disease in numerous piglets and pregnant sows. A deposit of the isolated viral agent was made on Jul. 18, 1991, with the American Type Culture Collection in Rockville, Md. under the accession number ATCC-VR2332. The viral agent is a fastidious, non-hemagglutinating enveloped RNA virus.

The wild-type virus is preferably modified to a substantially avirulent form by inoculating the virus on a full or partial sheet of simian cells in the presence of serum in a suitable growth medium; incubating the inoculated cell sheet at a temperature from about 35° C. to about 37° C. until a cytopathic effect is observed and repeatedly passaging the virus through the simian cell line on maintenance medium in the presence of serum and under appropriate passaging conditions.

The vaccine includes a carrier agent, such as sucrose gelatin stabilizer, which is mixed with a live modified virus that is produced as described above. The vaccine is preferably used to prevent PRRS by immunizing swine via the local (upper mucosal) route or parenteral route of vaccination. The immunized swine typically remain free of disease symptoms subsequent to being challenged with the wild-type virus.

The vaccine may be produced in commercial quantities by a process including the steps of preparing expansion cultures of a simian cell line; preparing production cultures by infecting the expansion cultures with an attenuated virus; harvesting the production cultures; stabilizing and lyophilizing the virus.

BRIEF DESCRIPTION OF THE DRAWING

FIG. 1 is a process schematic diagram for use in making commercial quantities of the PRRS vaccine.

DETAILED DESCRIPTION OF THE PREFERRED EMBODIMENT

The following non-limiting examples set forth preferred methods and materials for use in practicing the present invention.

EXAMPLE 1
Isolation, Identification and Attenuation of the PRRS Virus, and Production of a Modified Live Vaccine

A. Isolation and Identification

A tissue homogenate was obtained from piglets in PRRS-infected herds. This homogenate consistently reproduced the respiratory and reproductive forms of PRRS when intranasally inoculated in gnotobiotic piglets and pregnant sows. Gnotobiotic piglets so inoculated with either unfiltered or filtered (0.45, 0.22, or 0.1 µm) inoculum became anorectic and developed microscopic lung lesions similar to lesions seen in PRRS-affected herds. The same inoculum also caused reproductive failures identical to those seen in PRRS-infected herds.

The tissue homogenates from which the virus was isolated included lung tissue (Group 1) and combined brain-spleen-liver-kidney tissues (Group 2) obtained from an infected piglet in a PRRS-infected herd. The separate homogenate groups were each centrifuged at 4000×g for 25 minutes. The resultant supernatant was collected and filtered using a 0.45 micron sterile syringe filter. The filtered supernatants were then combined. One ml of the combined filtered supernatant was used as inoculum to infect each of the respective cell lines as described below.

The filtered supernatant was added to a growth media including a cell line as described below, modified Eagle's medium ("MEM") from JRH Biosciences and gentamicin at about 100 µg per ml.

Two tests were conducted for each cell line using 75 ml plastic bottles. In Test Number 1, the filtered supernatant was inoculated into two bottles each having a full cell sheet of each of the cell lines listed below. Additionally, about 2.5 mg of trypsin was added to this first bottle. All other remaining conditions were the same for each culture bottle.

In Test Number 2, the combined tissue homogenate material was inoculated into bottles containing the same cell lines as used in Test Number 1; however, the cell sheets were only 20–40% confluent at the time of inoculation. The media additionally contained about 10% fetal calf serum, which was not present in the media of Test 1. The inoculum was again administered in an amount of about 1 ml, and the cultures were incubated at about 34° C. for approximately seven days.

All of the bottles were incubated for about seven days at approximately 34° C. The results were recorded at the end of about seven days. After freezing and thawing, a sample was taken for a second passage in the same cell line. The remaining material was frozen in liquid nitrogen and stored at about −60° C. The results of both Test Number 1 and Test Number 2 are summarized below in Table 1:

TABLE 1

Testing Cell Lines for Viral Host

| Cell Line Used | Test Number 1 | Test Number 2 |
| --- | --- | --- |
| Bovine Turbinate (BT) | − | − |
| Feline Kidney (CRFK) | − | − |
| Monkey (Vero) Kidney | − | − |
| Monkey (Vero) Lung | − | − |
| Canine Kidney (MDCK) | − | − |
| Porcine (PK₂A) Kidney | − | − |
| Mink Lung | − | − |
| Ferret Lung | − | − |
| Bovine Lung | − | − |
| Buffalo Lung | − | − |
| Bovine kidney (MDBK) | − | − |
| Swine Testicle (ST) | − | − |
| Monkey Kidney (MA-104) | − | + |
| Human Rectal Tumor (HRT-18) | − | NT |
| Human Lung | NT | − |

+ = CPE Effect
− = No CPE Effect
NT = Not Tested

No cytopathic effect ("CPE") was observed in Test Number 1 in any of the cell lines evaluated. In Test Number 2, however, small clumps of MA-104 cells began to swell and form "weak holes" in the monolayer around the edges of the bottle. Fluid was separated from the bottle, and passed into a new bottle of MA-104 cells (again 20–40% cell sheet), and then subsequently passed a third time. This apparent CPE became stronger with each passage. Passage 3 retained its virulence. This passage was deposited with the American Type Culture Collection in Rockville, Md. under Accession No. ATCC-VR2332.

The ATCC-VR2332 virus consistently causes clinical PRRS symptomology, pulmonary lesions in gnotobiotic pigs, and positive ImF results. Thus, the ATCC-VR2332 virus may represent an unidentified genus of the Togaviridae. ATCC-VR2332 virus is also not a known pathogen of swine, because specific antisera to several common viral pathogens of swine failed to either neutralize the virus or detect antigens in infected cells.

The ATCC-VR2332 virus is a fastidious non-hemagglutinating enveloped RNA virus. The ATCC-VR2332 virus grows in a continuous cell line, specifically MA-104 and other simian cell lines. The ATCC-VR2332 virus grows to high titers ($10^7$ $TCID_{50}/1$ ml) on the commercial cell line MA-104.

The ATCC-VR2332 virus contains a lipid envelope as indicated by the loss of infectivity following treatment with chloroform. A lipid envelope could also be visualized as an electron translucent ring surrounding the empty particles. The morphology of the PRRS virus is not distinctive on direct electron microscopy (DEM) and would be extremely difficult to identify in preparations containing cellular debris. The morphology of the gradient-purified ATCC-VR2332 particles and the average diameter of 62 nm are very similar to virions of equine Arteritis and lactic dehydrogenase viruses.

The equine Arteritis virus has a reported size range of 50–73 nm, which is similar to the 48–84 nm size for the ATCC-VR2332 virus. 30–35 nm cores in several particles of ATCC-VR2332 were observed, which cores resemble the nucleocapsid cores described for equine Arteritis virus. Thus, morphologically, ATCC-VR2332 most closely resembles the Arteritis virus group.

The presence of an RNA genome in ATCC-VR2332 was confirmed by the ability of this virus to continue to replicate in the presence of 5-bromo-2 deoxyuridine and mitomycin C, which are known to inhibit the replication of DNA and one family of RNA viruses (Retroviridae), but not other RNA viruses. Nevertheless, the provisional classification of ATCC-VR2332 virus as an RNA virus agrees with the observation that this virus replicates in the cytoplasm of the cell as indicated by the presence of virus antigens detected by ImF. Also, Actinomycin D, which interferes with DNA-dependent RNA transition, has no effect on the replication of the ATCC-VR2332 virus. These results indicate that ATCC-VR2332 virus does not require nuclear functions for replication.

In summary, the size, morphology, presence of an RNA genome, and other biologic properties tentatively place ATCC-VR2332 virus in the family Togaviridae. ATCC-VR2332, however, could not definitely be placed in a known genera of this family. Although, morphologically, ATCC-VR2332 virus closely resembles the arteriviruses, the virus should not be placed in a definite genera until additional information on the RNA and protein structure are available.

B. Attenuation

The harvest from VR2332 passage 3 was subjected to two additional passages described in detail below, and the harvest from passage 5 was sent to an outside laboratory for purification. Specifically, the ATCC-VR2332 virions were identified after purification in CsCl gradients (centrifuged at 200,000×g) following extraction with 1,1,2-trichlorotrifluoroethane. The purified virions were labeled with an immuno-gold kit utilizing anti-ATCC-VR2332 hyperimmune sera and gold conjugate. The buoyant density of the ATCC-VR2332 virions in the CsCl gradients was 1.18–1.19 g/ml. Sucrose gradients consistently resulted in loss of virus titer and were abandoned as a suitable gradient for purification.

The purified passage 5 harvest was thereafter subjected to an additional 65 passages as detailed below. The resultant harvest from passage 70 was attenuated and was designated as the Master Seed Culture. This avirulent Master Seed Culture was deposited with the American Type Culture Collection under Accession No. ATCC VR-2495. Finally, an additional 5 passages were conducted to obtain ATCC VR-2332 passage 75 (additional passages could also be conducted if desired).

Passages 4–75 of the ATCC VR2332 virus were conducted in a host tissue culture stock of commercially available MA-104 Green Monkey kidney cell line. This tissue culture stock was prepared as follows. A growth medium was prepared to include a mixture of Eagles Minimum Essential Medium ("MEM") from JRH Biosciences (catalog #200–2041), and 10% fetal calf serum from JRH Biosciences. About 1 ml of ATCC-VR2332 inoculum was added to a 75 cubic centimeter bottle containing 50 ml of this growth medium. The bottle was held for about 7 days and incubated at a temperature ranging from about 35° C. to about 37° C.

Tissue culture stock bottles were prepared by expanding the resultant incubated culture, which was split 1:4 in the following manner. The growth media, which had a volume of about 50 ml, was decanted. The cell sheet was removed by adding 10 ml of trypsin-versene 1×, and incubating at 37° C. for 5–10 minutes. Subsequently, the cells were removed from the bottle and centrifuged at 270×g for 5–10 minutes. The supernatant the decanted and the pellet was resuspended in 5–10 ml of MEM media including 10% fetal calf serum as before. The cells were placed into 200 ml of growth media, which was then subportioned into four 75 ml bottles at 50 ml per bottle, thereby achieving the 1:4 split.

The resultant cultures were maintained at a temperature ranging between 35–37° C. until they could be used. After about 3 to 4 days of incubation, the bottles had developed a full cell-sheet coating, and were ready for use.

The PRRS virus ATCC-2332 was propagated in the MA-104 continuous cell line cultures that were produced as described above. The pH of the culture media was adjusted to 7.2, and the cultures were incubated at a temperature ranging from about 35° C. to 37° C. The virus was inoculated onto the MA-104 cells by adding about 1 ml of a frozen inoculum from the preceding passage to the fluid growth media. The virus was allowed to absorb onto the cells for 24 hours.

The growth media was decanted about 24 hours after inoculation with the ATCC-VR2332 virus, and the flask was refilled with 50 ml of a maintenance media substituting 4% fetal calf serum for the 10% fetal calf serum content of the growth media. The maintenance media had a pH of 7.6. Subsequent to this media changeover, the culture was incubated at a temperature of between 35–37° C. The virus was allowed to grow until about 50–60% of the MA-104 cell sheet in the culture was destroyed by the virus. The sample was then frozen in liquid nitrogen, and prepared for passage onto another flask of MA-104 cells.

The cross-reactivity of passages 3–70 was also demonstrated. The PRRS VR-2332 passage 3 virus was used to immunize swine, rabbits and goats to produce anti-sera to PRRS. The serum was used to neutralize PRRS virus at various passage levels from passage 3 through passage 70. In addition, two monoclonal antibodies (SDOW-12 and SDOW-17) were prepared using spleenic lymphocytes from mice immunized with VR-2332 PRRS virus. The monoclonal antibodies were show to react against all U.S. and European isolates of PRRS as of December, 1992. The monoclonal antibodies were used to identify or detect PRRS virus passages 3–70.

C. Production of Modified Live Vaccine

Two vaccine preparations were formulated incorporating, respectively, the Master Seed Culture (the harvest from ATCC VR-2332, passage 70) and the harvest from ATCC VR-2332, passage 75. The Master Seed Culture virus and the passage 75 virus are substantially avirulent i.e., the vaccines when administered to swine or other mammals prone to PRRS contacts, fails to cause clinical signs of PRRS disease, but is capable of inducing an immune response that immunizes the animal against pathogenic forms of the PRRS virus. The vaccine was produced by conventional means. Normal stabilizers and carriers were added prior to lyophilization.

EXAMPLE 2 in vivo Testing of the Viral Isolate

The virulent third passage harvest of the ATCC-VR2332 virus from Example 1 was used to inoculate two three-day old gnotobiotic piglets. Both piglets were exposed intranasally, one with 1 ml and the other with 2 ml. The piglets were clinically observed for seven days, then were euthanized and necropsied.

Tissue samples were collected from each piglet for histopathy and for recovery of the viral agent. The histopathology report confirmed that lung lesions in the infected piglets were identical to lung lesions from piglets known to have PRRS. The tissue samples were processed as in Example 1, and then cultured on 20–40% and 100% monolayer of the MA-104 cell line with bovine fetal serum. The viral agent was again recovered.

The third passage viral harvest was also used to inoculate sows in order to verify that the reproductive effects of the disease can be duplicated and confirmed. Two multiparous sows were inoculated intranasally at about 93 days of gestation. The sows delivered litters with 50% stillborn piglets (8/13 and 6/14 stillborn/live) on days 112 and 114 of gestation, respectively. Seven of the stillborn piglets were partial mummies and the liveborn piglets were weak and failed to nurse vigorously. The viral agent was recovered from tissues of the stillborn piglets in the manner of Example 1.

The viral agent was recovered from three herds known to have PRRS. Antibody titers to the ATCC-VR2332 agent have been identified in these same herds.

EXAMPLE 3

The purpose of this study was to determine the minimal protective dose of the PRRS virus (VR-2332 passage 75)

selected for use as a modified live virus vaccine. This was done by analyzing the degree that two selected vaccine dosages (4.0±0.5 logs/dose and 2.0±0.5 logs/dose) were able to control the onset of abnormal conditions following challenge with virulent PRRS virus (VR-2332 passage 3, 3.5±0.5 logs/dose) and comparing vaccinated-challenged pigs with unvaccinated-challenged and unchallenged (normal) pigs. The modified live vaccine was produced using passage 75 virus as explained previously.

Sixty-two seronegative piglets were selected for use from the source farm and distributed into four study groups, designated groups 1, 2, 3 and 4. Twenty-one piglets in group 1 were vaccinated with 2.0 ml PRRS vaccine L-4 intramuscularly (4.0 logs/dose). Twenty-one piglets in group 2 were vaccinated with 20 ml PRRS vaccine L-2 (2.0 logs/dose). Ten piglets in group 3 and ten piglets in group 4 were not vaccinated. The piglets in control groups 3 and 4 were housed in separate facilities to insure susceptibility to the challenge virus. Groups 1, 2 and 3 were challenged with 2.0 ml PRRS virus VR-2332 passage 3 intranasally on trial day 28. The piglets of group 4 were not challenged. The pigs in all four study groups were observed and monitored regularly during the 31 day pre-challenge period and the 21 day post-challenge period. Parameters used to evaluate the studies were clinical symptoms, body weight, body (rectal) temperature, white blood cell count, virus isolation and serology. Efficacy of the vaccine was demonstrated by reducing the number of days the vaccinated pigs were viremic, by preventing leukopenia and fever and by maintaining normal growth rate following challenge.

Body (rectal) temperatures were measured prior to and following vaccination. The group average temperatures for group 1 increased on 2 DPV and 3 DPV while group 2 increased on 3 DPV. The duration of the temperature rise for either group was short, 2 days for group 1 and 1 day for group 2.

Neither of the vaccinated groups experienced a drop in white blood cell counts following treatment. Previous studies have indicated that exposure to virulent PRRS virus would cause a leukopenia within 72 hours following exposure.

The results of measuring weight gain during the post vaccination period indicated that the treatment did not adversely affect the performance of the vaccinated pigs. During the 29 days following vaccination, the weight gain by either of the vaccinated groups was not significantly different at the confidence level of 0.05 from the weight gain of groups 3 and 4.

The clinical observations showed little deviation from the norm in most categories except for feces and nostrils. Comparing the fecal scores of the vaccinated groups with the scores of the combined control groups (groups 3 and 4) using a two-tailed t-Test showed no significant difference at the 0.05 confidence level. The p value between group 1 and the combined control groups was 0.47, while that between group 2 and the combined control group was 0.87. Comparison of the nostril scores between group 1 and the combined control group had a p value of 0.41. Only two out of 21 pigs in group 2 were observed to have clinical scores for nostrils. The t-Test analysis for the total individual clinical scores of groups 1 and 2 with those of the combined control group showed a p value of 0.53 and 0.74 respectively. These comparisons demonstrate the lack of difference between those animals receiving vaccine at either dose level and the non-vaccinated controls.

The results of the virus isolation from blood indicated that 100% (21 out of 21) of group 1 became positive while group 2 had 90% (19 out of 21) tested positive. Throughout the post vaccination period, the control groups 3 and 4 remained negative. The results of the (Immunoperoxidase Test) IPT assay provided a similar picture in that 100% of group 1 became serologically positive as did 90% of group 2. Both groups remained negative for serum neutralizing antibodies through 21 DPV. Neutralizing antibody was detected in both groups at 29 DPV (0 DPC—see post challenge results). The control groups remained serologically negative by both test procedures up to the time of challenge.

The analysis of the post vaccination observations indicate that there appears to be no adverse effect resulting from treatment with either vaccine dosage used in the study. However, the higher dosage did serologically convert all (21 out of 21) pigs while the lower dosage converted 19 out of 21 pigs or 90%.

Following challenge with a virulent PRRS virus, the clinical parameters that were monitored in the vaccinated and non-vaccinated challenge groups provided evidence of protection by the two vaccine doses tested. The results of testing for viremia provided clear evidence of the benefit of the vaccine. The non-vaccinated group (group 3) was 100% viremic on 3 DPC, 5 DPC and 7 DPC while the incidence of viremia for the same observation days in group 1 (3.65 logs/dose) and group 2 (1.85 logs/dose) was 15, 5 and 10% and 30%, 20% and 15% respectively. Also, no virus was recovered from blood samples in group 1 after 9 DPC and from group 2 after 13 DPC, while 30% of group 3 was still positive on 19 DPC.

The results of monitoring body (rectal) temperatures also provided evidence of the efficacy of the vaccines. During the 21 day observation period, the average temperature of group 3 exceeded 104° F. on 5 days. The average temperatures of groups 2 and 3 did not exceed 104° F. Furthermore, the average temperature of group 3 exceeded 104.5° F. on two days, 2 DPC and 6 DPC.

Following challenge, the results of the white blood cell counts showed group 3 experiencing leukopenia that had a 16% drop occurring on 5 DPC. Neither of the vaccinated groups experienced a drop greater than 6% throughout the observation period.

Monitoring the various treatment groups' weight gains during the 21 days following challenge showed that vaccination with either dose level maintained a normal growth rate. The two vaccinated groups, 1 and 2 had an average percentage weight gain of 74 and 73 respectively. Group 4, the normal control animals, had a group average weight increase of 75%. In contrast, the group average percentage weight gain in group 3, the non-vaccinated-challenged controls, was 69%. This was significantly different from groups 1, 2 and 4 at P=0.009 using a two-tailed t-Test and a confidence level of 0.05.

Although the results of the clinical tests may not be as definitive in demonstrating the efficacy, they still illustrate the benefits of the vaccines. Following challenge, groups 1, 2 and 3 showed a significant increase in the incidence of respiratory symptoms. The daily average individual animal score for groups 1, 2 and 3 was 0.39, 0.64 and 0.53 respectively. This illustrates the benefits of the higher dose (3.65 logs/dose) over the lower dose (1.85 logs/dose) and no vaccination. Although fecal observations were dramatic following challenge, they were not significantly different (using a confidence level of 0.05) from the observations following vaccination and prior to challenge. Thus, in this experiment the challenge with virulent PRRS virus appeared not to have an effect on the lower gastrointestinal tract.

Overall, the remaining clinical observations did not exhibit a significant change as a result of the challenge. For the parameters of nostrils and mouth in group 1, one pig had 25% of the total group nostril score and another pig had 94% of the group score of the mouth category. Similarly, in group 2, one pig had 22% of the group nostril score and another pig had 43% of the group mouth score. Overall, the incidence of post challenge clinical observations for these two parameters was not significantly different from the post vaccination observations. Similar conclusions can be drawn about these two clinical parameters for group 3. Group 4 remained relatively normal throughout the body.

At the end of the observation period, all pigs were euthanized and the lungs were observed macroscopically for signs of pathological involvement. Sixty percent (6 out of 10) of group 3 exhibited noticeable involvement. In comparison, 10% of group 1 and 19% of group 2 appeared to have noticeable involvement. When compared to group 4, the normal controls, 80% of group 1, 81% of group 2 and 30% of group 3 were described as being not observably different.

Virus isolation from lung tissues was performed. No virus was isolated from lung tissues of group 1 pigs. One sample of the 21 pigs of group 2 was positive for virus. Virus was isolated from three of ten samples of group 3 pigs and none from group 4.

The conclusion drawn from these results is that both dosage levels (3.65 logs/2.0 ml dose and 1.85 logs/2.0 ml dose) of a modified live PRRS virus vaccine containing VR-2332 passage 75 were efficacious against the respiratory disease in 3 to 5 week old pigs that were challenged at 29 DPV with virulent PRRS virus.

This study indicated that the preferred minimal protective dose is 3.65 logs/2.0 ml dose. In several parameters used to evaluate the efficacy of the vaccine dosages, such as viremia, clinical respiratory signs, lung pathological involvement and virus isolation from lung tissue, those animals vaccinated with the higher dose were better protected. Also 21 out of 21 pigs vaccinated with 3.65 logs/dose seroconverted by 21 DPV. In comparison, only 19 out of 21 pigs vaccinated with the lower dose had seroconverted by 29 DPV (0 DPC).

EXAMPLE 4

In this example, the duration of immunity using the PRRS passage 75 modified live vaccine described in Examples 1 and 3 was investigated. A fattening pig normally reaches slaughter weight at six months of age. In this example, the pigs were vaccinated at approximately 1 month of age (4–5 weeks old) and then challenged at 110 days post-vaccination. This duration of immunity would then cover most of the expected life span of normal fattening pigs.

Sixty-two PRRS seronegative piglets were obtained and distributed into four study groups, designated Groups 1, 2, 3 and 4. Twenty-one pigs in Group 1 were vaccinated with 2.0 ml of PRRS-MLV passage 75 vaccine having 3.32 logs per dose. Twenty-one pigs of Group 2 were vaccinated with 2.0 ml of this vaccine having 1.64 logs per dose. The 10 pigs in Group 3 and Group 4 were not vaccinated and were housed in separate facilities to maintain seronegative status. At the termination of the study described in Example 3, the Group 2 pigs for this example were removed from the study and euthanized since it was concluded that the minimal protective dose was 3.68 logs and not 1.87 logs per dose. Groups 1 and 3 were challenged intranasally at 110 days post-vaccination (DPV) using VR-2332 passage 3 virus (3.9 logs/ml). The pigs of Group 4 were not challenged. The pigs were monitored for 21 days post challenge (DPC) for clinical symptoms, change in body weight, body (rectal) temperature, white blood cell counts, viremia and serology. Protective immunity at 110 days post-vaccination was demonstrated by absence of viremia, prevention of leukopenia and fever and improved weight gain as compared to challenged non-vaccinated pigs.

Following vaccination, the vaccinated pigs were monitored for any adverse reactions to the vaccine. The parameters that were monitored included body (rectal) temperature, white blood cell counts, weight gain, clinical symptoms, serology and viremia.

Body (rectal) temperatures were monitored daily from −1 DPV through +4 DPV. The analysis of the group averages showed no significant increase in the treatment groups' temperatures as a result of the vaccine. The vaccinated pigs of Group 1 experienced a maximum rise of 0.2° F. as compared to the pre-vaccination average.

White blood cell counts were monitored at various time points before and following the administration of the vaccines. Group 1 experienced a 14% drop when compared to the pre-vaccination average on 4 DPV. All other decreases in counts for Group 1 remained less than 9%. The remaining groups (3 and 4) did not experience any drops in WBC counts greater than 11% during the post-vaccination observation period.

The results of the weight gained from 0 DPV through 28 DPV were conflicting in that the change in weight by Group 1 was significantly different from group 4 (P=0.02). There is no explanation for this difference since all other parameters that were monitored showed no major differences between Group 1 and Group 4.

Statistical analysis of the post-vaccination clinical scores indicated no difference between the vaccinated groups and the non-vaccinated control groups. Although the fecal score had the highest incidence, there was no significant difference between Group 1 and Groups 3 and 4, P=0.75, P=0.59, respectively. Likewise, clinical nostril scores were not significant. The comparison between Group 1 and Group 3 had P values greater than 0.8. The p value for the comparison between Group 1 and Group 4 was 0.02, with Group 4 having the higher incidence. None of the other clinical parameters showed a significant rate of occurrence.

The post-vaccination serological results indicate that the vaccine dosage successfully immunized the treated animals. At 14 DPV, Group 1 had 48% testing positive by the IPT assay. Seven days later at 21 DPV, 100% of the treatment group tested positive by IPT. Group 1 remained negative for serum neutralizing (SN) antibody up to 28 DPV. All pigs in Group 1 remained serologically positive by both assays up to the time of challenge at 110 DPV. Pigs of Groups 3 and 4 remained serologically negative throughout the post-vaccination period.

The post-vaccination virus isolation results indicated that 100% of the treatment group were successfully inoculated. This supports the serological data previously described. Both control groups 3 and 4 remained negative for the duration of the post-vaccination observation period.

The post-vaccination observations indicate that the treatments did not have any severe undesirable effects on the treated animals and the control animals remained free of PRRS virus.

Following the challenge with virulent PRRS virus, various clinical parameters were monitored to evaluate the benefit of the vaccine treatment. The vaccinated group (Group 1) was compared with the non-vaccinatedchallenged group (Group 3) and non-vaccinated-non-challenged group (Group 4).

The post-challenge serological results demonstrated that the level of challenge successfully stimulated an immune response in Group 3. Group 1 did not experience an anamnestic antibody response following challenge with the virulent virus. The serological results indicated Group 4 remained negative throughout the observation period of 21 days.

The most dramatic findings were the virus isolation results. One hundred percent of Group 3 tested positive at 3, 5 and 7 DPC and as late as 21 DPC, 20% of this group were testing positive. Group 1 was negative at 0 DPC and remained so throughout the 21-day observation period. An unexpected result was the positive isolation of PRRS virus from blood samples from Group 4. The first positive virus isolation from Group 4 occurred at 15 DPC. This observation correlated with other parameters that will be discussed later. Even though Group 4 had come into contact with the PRRS virus, the data collected should still be considered valid since the apparent exposure took place during the latter third of the observation period and the primary interval of concern is from 1 DPC through 11 DPC. It is during this time that which the majority of the comparisons between Groups 1 and 3 were being made. The most important result was the apparent prevention of infection, as shown by lack of virus isolation in the vaccine treatment group.

The importance of the post-challenge clinical scores appear to be limiting in evaluating the effect of the vaccine treatment. Although clinical respiratory signs were observed in Groups 1 and 3, the signs were not evenly distributed. In the case of Group 1, two pigs accounted for 88% of the total score for the group. Likewise, two pigs in Group 3 accounted for 71% of the group total score of 49. The total fecal score of Group 1 is significant when compared to the other groups. However, only 9 of 21 pigs were observed to have any clinical signs in this category and of the 9 pigs, 3 pigs accounted for over 55% of the total score for the group. No fecal scores were attributed to Group 3 and only 1 pig in Group 4 was observed to have clinical fecal signs. The clinical scores for nostrils and mouth may have limited importance without being associated with other parameters such as respiratory. The incidence of nostril observations was limited in both Groups 1 and 3 having less than 50% of each group having a score. The scores for mouth observations had a high incidence with 90% of Group 3 and 76% in Group 1. There was no significant difference between these two groups for mouth clinical scores, P=0.45. All other clinical parameters were observed to be normal.

During the post-challenge observation period, Group 1 gained an average of 42.62 pounds. Group 3 had an average weight gain of 36.5 pounds and Group 4 gained an average of 37.1 pounds. There was no significant difference between Groups 3 and 4, P=0.9, and this may have been a result of Group 4 having been accidentally exposed to the PRRS virus. However, this does not diminish the comparison of data between Group 1 and 3 because there was a statistically significant difference between those two groups. Evaluating performance of pigs over a time provides an excellent tool to evaluate the overall well being of these pigs. This data in conjunction with the other parameters indicate the benefit of the vaccine being tested in the face of an experimental challenge.

The post-challenge temperatures demonstrated the benefit of the vaccine treatment in the face of an experimental challenge. The challenge control group, Group 3, had 8 days in which the group average temperature had at least a 1° F. rise over the pre-challenge average. Group 1 did not have group average rise of 1° F. at any time. Although Group 4 was contaminated with the PRRS virus, the group average temperature did not increase by a degree. This was due to the spread of the virus within the group being gradual and not totally encompassing as compared to the experimental challenge. However, the analysis of individual pig temperatures from 15 DPC through 21 DPC showed Group 4 pigs experiencing temperature rises following exposure to the PRRS virus. The analysis of the individual pig temperatures in Groups 1 and 3 further emphasized the benefit of the vaccine treatment. Ten of 10 pigs in Group 3 experienced a 1° F. rise on two consecutive days or more. In contrast, the pigs of Group 1 did not have comparable results.

Further evidence of the efficacy of the vaccine was demonstrated by the results of the post-challenge WBC counts. Group 1's average WBC count decreased following challenge. Decreases of 14%, 19%, 14%, 21% and 13% occurred on days 1, 3, 5, 7 and 9 following challenge, respectively. On the same test days, Group 3 had average decreases of 15%, 37%, 43%, 31% and 28%. Group 4, the non-challenge control group, experienced drops of between 11% to 17% during the same time period. Analyses of the individual pigs' counts further substantiate the protection provided by the vaccine treatment. Ten of 10 pigs in Group 3 experienced a 25% drop or greater in WBC counts on two or more consecutive test days. Group 1 had 2 of 21 experiencing leukopenia of 25% or greater on two consecutive days. The infected pigs of Group 4 experienced similar results to that of Group 3. The incidence of leukopenia became apparent as the spread of virus progressed through the group. Between 15 DPC and 21 DPC, 50% of the group experienced WBC count decreases of 25% on consecutive test days. These results indicate that the vaccinated pigs did not experience the leukopenia that the non-vaccinated pigs did.

The analysis of the gross (macroscopic) observations of the lungs at 21 DPC were divided into parenchyma and pleura scores that were then combined for the total lung score. The analysis of the observations was made more difficult with the accidental PRRS virus exposure to the non-challenged control group, since a negative base line could not be developed. Thus it is necessary to limit the comparison between Group 1 and 3 since both groups had exposure to the same virus challenge and at the same time. The parenchyma scores for Group 3 were greater in severity with 4 of 10 pigs having individual scores of 200. The highest score in Group 1 was 100. Both the percentages of the treatment group affected and the severity of the parenchyma lesions were decreased with the vaccine treatment. Similarly, vaccine treatment decreased the incidence and the severity of the pleural lesions. Group 1 had 24% (5 of 21) having pleural scores of 100; while Group 3 had 50% (5 of 10) having pleura scores of 100. The majority of the pigs (9 of 21) in Group 1 had incidental pleural scores of 15 or less. The correlation of the lung scores with respiratory problems was nonexistent. For example, one pig of Group 3 had clinical respiratory score 23 and a total lung score of 287.5; while another Group 3 pig had clinical respiratory score of 0 and a total lung score of 300. There are several additional examples of the lack of correlation between the lung score clinical respiratory scores. Whether or not macroscopic observations are valid to analyze the beneficial effect of the vaccine, it can be concluded that the treatment group, Group 1 had fewer animals with lesions and the severity of those lesions was decreased.

In conclusion, many of the parameters used to evaluate the effect of the vaccine in the face of an experimental challenge at 110 days post-vaccination correlated well with each other. During the period (3–9 DPC) in which viremia is the most evident, a significant leukopenia and a rise in body temperature occurred. At the time of challenge, the pigs were approximately 20 weeks of age or 12 weeks older than the age of pigs challenged in Example 3. Many of the clinical symptoms noted in this study were more severe. For example, the rise in body (rectal) temperature was elevated for 8 days in this study as compared to 5 days in the Immunogenicity Study. The severity of the leukopenia experienced by the non-vaccinated-challenged control group (Group 3) in this study was much more dramatic than by the challenge control group of the Immunogenicity Study. In the former study, the challenge control group experienced decreases in WBC counts of 43% to 27% (3–9 DPC). In the Immunogenicity Study, the challenge control group experienced decreases of 15–21% from 2–9 DPC. The number of days in which viremia was detected during the post-challenge period (1–14 DPC) for the vaccinated challenged group of the Immunogenicity Study was 0 out of possible 110 days as compared to 45 of 110 days in the challenged control group in this study. Thus, the increase in the severity of the clinical signs was not entirely due to increase in the duration of viremia.

The post-challenge results of this study demonstrated that vaccination with PRRS-MLV vaccine having the dosage level of 3.32 logs per 2.0 ml provided protection against a challenge with virulent PRRS virus at 110 days post vaccination. They are: (1) The vaccinated animals were entirely negative for viremia during the 21 day post challenge observation period. (2) Apart from minor occurrences of respiratory, fecal, nasal and oral clinical signs, the vaccinated pigs were observed to be normal for clinical signs. (3) The weight gained by the vaccinated pigs was significantly greater than the amount gained by the non-vaccinated-challenged pigs. (4) The vaccinated pigs did not experience a notable rise in body temperature. (5) No remarkable decrease in the WBC counts occurred in the vaccinated pigs. (6) The occurrence and severity of parenchyma and pleura lesions were less in the vaccinated pigs.

EXAMPLE 5

In this example, the PRRS-MLV passage 75 vaccine described in Examples 1 and 3 was tested to determine the onset of immunity. Seven days prior to initiation of the study, 35 pigs were tested for PRRS antibody using the Immunoperoxidase Test (IPT) and for the presence of PRRS virus in the blood stream by virus isolation on MA-104 cells. Ten pigs in Group 1 were vaccinated intramuscularly with 2.0 ml of PRRS-MLV passage 75 vaccine on trial day 0. Ten pigs in Group 2 were vaccinated in the same fashion on trial day 7. Ten pigs of Group 3 and 5 pigs of Group 4 were maintained in separate facilities, but in similar environmental conditions and served as non-vaccinated contemporary controls. Pigs in Groups 1, 2 and 3 were challenged on trial day 14. The challenge inoculum, consisting of virulent PRRS virus (VR-2332, passage 3, 3.7 $\log_{10}$ virus per 1.0 ml), was administered intranasally (2.0 ml/pig). Pigs of Group 4 remained unchallenged. All pigs were monitored for 10 days for clinical signs of respiratory disease. All pigs were euthanized at the conclusion of the study for evaluation of lung lesions.

At the time of challenge, the pigs of Group 1 were serologically positive by IPT assay but not for serum neutralizing activity. In contrast, all the other pigs including those in Group 2 were negative by both procedures. Fifty percent of Group 2 pigs tested positive by IPT at 7 DPC and 100% at 10 DPC. The pigs of Group 3 tested positive by IPT at 10 DPC. One pig from each of Groups 1 and 2 developed SN activity at 10 DPC and 7 DPC, respectively. The SN results are not significantly different at $p=0.05$ level. The results of this study demonstrated that protection was elicited as a consequence of the treatments even though the pigs at the time of challenge were either serologically negative or without serum neutralizing activity. Protection may not be directly linked to humoral immunity. Cell mediated immunity in response to vaccination with a modified live vaccine can play a major role in protection against a virulent challenge.

In Example 4, the lack of viremia following challenge was an important criterion to demonstrate protection by vaccination. However, with the short period between vaccination and challenge in the present study the vaccinated animals had not resolved post-vaccination viremia. Also, since the challenge was a homologous challenge, it was not possible to differentiate the challenge virus from the vaccine virus. Four pigs of Group 1 and 1 pig from Group 2 tested negative for viremia for at least one test point from 3 DPC through 9 DPC. One hundred percent of Group 3 tested positive for viremia during the same time period.

Unlike previous examples, the significant appearance of clinical respiratory signs were detected in this study. Group 3 had 9 of 10 animals experiencing respiratory difficulties on one or more days (average number of days equaled 3.6). The number of animals for Group 1 and 2 experiencing breathing difficulties for one or more days was one and zero, respectively ($p<0.001$). The incidence of clinical signs for nostrils was similar to that of respiratory signs. Group 3 had 8 of 10 experiencing clinical signs for nostrils on one or more days. The average duration of clinical signs was 3.1 days. In contrast, Group 1 and 2 were significantly different with average duration times of 1.3 days and 0.1 days, respectively ($p<0.001$). The occurrences of the remaining clinical parameters were uneventful.

Both of the vaccinated groups gained more weight than the challenge control group. Group 2 gained an average of 10.6 pounds during the 10 day observation period as compared to 7.8 pounds for Group 3 ($p=0.01$). The average gain for Group 1 was 9.6 pounds which was not significantly different compared to Group 3. This group had the two smallest pigs, which weighed 7 and 12.5 pounds, respectively, on trial day 0 and 6 and 12 pounds, respectively, at the time of challenge. The group average gain with the two smallest pigs removed is 12.3 pounds which is significantly different from Group 3 ($P<0.001$). The poor rate of gain by the two pigs may be attributed to their inability to compete with the larger pigs in the group. These pigs also experienced diarrhea during the post-challenge observation period. The pigs in Group 4 had an average gain in weight of 15.2 pounds during the 10 day period. An average daily weight gain of between 1.0 to 1.5 pounds would be expected in pigs of this age. These results demonstrate that the vaccination treatment at 7 and 14 days preceding the challenge provided protection, which allowed for an expected growth rate.

Following the challenge, the pigs of Group 3 had a sustained temperature rise of 1° F. over the pre-challenge average for an average of 4.6 days. The average number of days that the pigs in Group 1 and 2 had a comparable temperature rise were 0.5 and 1.1 days, respectively ($p<0.001$). Only 1, of the 20 vaccinated pigs had 1° F. rise on 2 consecutive days as compared to 8 of 10 in Group 3.

The statistical difference between the vaccinates and controls was p<0.001. These results demonstrated that the vaccine treatment of pigs in Group 1 and 2 prevented the occurrence of fever as the result of exposure to virulent PRRS virus.

The pigs of Group 3 experienced dramatic reduction in white blood cell counts on 3, 5 and 7 DPC. These results closely paralleled the temperature rise that these animals experienced during the same period. The pigs of the vaccinated groups had a mild leukopenia lasting 1–2 days before returning to pre-challenge values. The values for the vaccinated pigs were significantly different from the challenge controls, (p=<0.001). These results emphasized the level of protection provided by the vaccine treatment at 7 or 14 days before challenge by reducing the level and duration of leukopenia.

The vaccine treatment at either 14 days or 7 days before challenge reduced the severity of lung lesions. Both vaccinated groups were significantly different from the challenge control group (P=0.01). The vaccinated scores are similar to those for Group 4, the normal control group. The average lung score for Group 3 was 97.1 compared to 9.3 and 7 for Groups 1 and 2, respectively. The lesions observed in the latter two groups are considered to be normal and expected occurrences in healthy conventionally raised pigs.

The results in the present study demonstrated that protective immunity was stimulated within 7 days of vaccination with a modified live virus vaccine. Significant differences were observed in temperature response, weight gain, leukopenia, lung lesions and clinical signs following experimental challenge in the vaccinated pigs when compared to the non vaccinated-challenged pigs.

EXAMPLE 6

In this example, two groups (A and B) of 100 three-week old weaned pigs from a PRRS positive herd were vaccinated with either the PRRS-MLV passage 70 vaccine of Example 1 or a placebo (sterile water). Thirty pigs out of each treatment were monitored for adverse reactions by monitoring body temperature, weight gain and injection site reactions. These pigs and the remaining 70 pigs from each treatment group were also observed for signs of general health for 28 days following treatment. The results of this study demonstrate that the vaccine caused no side effects and is safe when used properly in a PRRS positive herd.

The pre-vaccinations (−2 DPV) rectal temperatures indicated that the pigs used in this trial were not normal healthy pigs. Group A's temperatures were significantly higher than those for Group B on trial days −2 and −1 (P<0.05). There were no significant differences between the two groups on trial days 0, 1, 2 and 3 (P<0.05). These results indicate that vaccination with the modified live PRRS vaccine did not exacerbate the conditions causing the existing elevated temperatures.

No pigs from either group experienced any post treatment reaction at the site of inoculation. These results further demonstrate the safety of the vaccine when administered in an approved manner.

During the 29 day period from trial days −2 through 27, the 30 pigs of Group A gained an average of 21.02 pounds and the 29 pigs of Group B gained an average of 18.18. This difference is significant at P<0.05. Since this trail was performed in the face of an active PRRS infection, the results are indicative of safety as well as efficacy.

The results of the clinical observations indicate vaccination significantly reduces the incidence of several clinical parameters. The reduced parameters include appearance from 62 to 6, feces from 48 to 24, eyes from 162 to 89, nostrils from 30 to 0, mouth from 30 to 0, appetite from 91 to 13, treatments from 37 to 14 and deaths 5 to 0. The decrease in the number of treatments received by Group 1 when compared to Group B was significant (P<0.05). The reduction of clinical sign provides further evidence that the modified live PRRS vaccine is safe when used in a herd that is experiencing a clinical outbreak associated with PRRS virus.

In conclusion, the vaccine was demonstrated to be safe when properly used in a herd that is experiencing an active clinical disease associated with a PRRS infection. The vaccine did not intensify the clinical symptoms whether they be associated with the PRRS virus or with secondary pathogens known to be present in this swine operation. Under the conditions that exist at this test site, these results also indicated a beneficial effect in the treatment group receiving the vaccine.

EXAMPLE 7

In this example, the effect of vaccination of 20 specific pathogen-free, mixed sex, Dutch landrace breed 5-week old piglets with a low dose of ATCC VR-2332 passage 75 vaccine (ATCC VR-2495) on the spread of Lelystad virus (LV) was determined. Wild strains of LV are believed important in predisposing pigs for secondary respiratory infections, causing bad performance and higher mortality rates. This example provides data regarding the effect of the vaccine on the transmission of the European antigenic type LV virus.

The pigs were separated into two 10-pig groups, one experimental group and one control group. Each experimental group pig was vaccinated intramuscularly with 2 ml of a diluted vaccine containing approximately $10^3$ $TCID_{50}$ of the ATCC VR-2332 passage 75 vaccine. Six weeks later, 5 animals from each group were challenged by intranasal inoculation with the wild type European strain of LV (Code CDI-NL-2.91, Ter Huurne, 5th Passage on Porcine alveolar macrophages) using a challenge dose of $10^{5.3}$ $TCID_{50}/2$ ml. After 1 day, the challenged pigs were returned to their pens.

The experiment tested whether, when and how many of the vaccinated and non-vaccinated pigs showed clinical disease or became viremic, and whether and how many of the contact-challenged penmates became infected with the Lelystad virus. The infection in the vaccinated and control group was then quantified and the transmission rates of the Lelystad virus in the vaccinated and control groups were calculated. For the vaccination to be successful, the severity and duration of disease and of viremia and the transmission rate in the vaccinated group must be smaller than in the control group.

This study, tested under the extreme conditions of low vaccine dose and heterologous challenge demonstrated the protective value of the vaccine.

Vaccination reduced the clinical signs of disease after challenge. It significantly reduced the mean rectal temperature after challenge; it significantly reduced the number of days the challenged pigs were viremic; and it significantly reduced the height of viremia in the challenged pigs. Furthermore, although transmission from direct-challenged to contact-challenged pigs did occur in all the pigs in the both the vaccinated and unvaccinated group, there was a significant difference in wild type LV transmission between the vaccinated and the unvaccinated group.

Vaccination with a low dose of the American antigenic type PRRS vaccine ATCC VR-2332 passage 75, was therefore effective in conferring protection against challenged with the European antigenic wild type Lelystad virus.

EXAMPLE 8
Commercial Scale Vaccine Production

FIG. 1 depicts a process schematic diagram for use in producing commercial quantities of the live modified Master Seed Culture virus from Example 1. Process P10 begins with step P12, which is the sterilization of all containers. Sterilization is preferably conducted by irradiation, but may also be done thermally or chemically. The types of containers include inoculum flasks, e.g., 75 to 150 ml, five liter flasks, roller culture vessels, and steel air-agitation bioreactor vessels.

Step P14 includes preparing expansion cultures of the host MA-104 cells. A stock of MA-104 cell line, at passage 58, is stored in liquid nitrogen and used to supply host cells for the viral culture through passage 78. Stock MA-104 cultures are grown in flasks ranging from about 75 ml to 150 ml in volume, and containing from 50 to 150 ml of medium. The medium preferably includes MEM mixed with 10% bovine or fetal calf serum and about 30 micrograms per ml of neomycin. The sterile flasks and media are preferably inoculated with about 1 ml of a prior-passage MA-104 culture, and incubated at from about 35° C. to about 37° C. for three to seven days.

Expansion of the stock cell cultures preferably occurs from a 150 ml flask to about 400–600 ml of media a ratio of 1:5 (volume to volume). After about 4–7 days of incubation at about 35–37° C., this 400–600 ml of media may then be subcultured to a five liter flask filled with media. Alternatively, the inoculum may be applied at a 1:3.4 ratio to a roller culture having about 670 to 850 cm$^2$ of growth area and 150 ml of medium, which is then subcultured to other roller culture vessels at a ratio of from about 1:9 to 1:11. The subcultures are incubated for about 4–7 days at about 35–37° C.

Step P16 includes preparing production cultures of virally-infected MA-104 cells. The expansion cultures of step P14 are typically further expanded to larger volume bioreactor vessels at a ratio of from about 1:3 to about 1:5 (volume to volume). The production vessels may include, for example, the five liter flasks of the expansion cultures or 40 liter stainless steel culture vessels equipped with an air lift agitator, temperature control, and pH control. The vessel is filled with an appropriate amount of growth medium, inoculated with MA-104 cells, incubated at about 35° C. for 4 to 7 days, and infected with the Master Seed Culture virus of Example 1. This virus will preferably have a titer of at least about 10$^6$ TCID$_{50}$ per ml by CPE, and will be added to the production vessel cultures at a ratio of at least about 0.1 to 10 ml to 100 ml of media. The production cultures are incubated at about 35° C. to about 37° C. for 2 to 3 days after infection with the attenuated virus.

Step P18 includes harvesting the production cultures of step P16 after the post-infection incubation period. The proper time for bulk harvest should be determined by observations of CPE as indicated by about 10% macroscopic changes (rounded cells and cell sheet degradation) or 10% pH change. The production culture of step P16 is harvested under a laminar flow hood by pouring into a sterile container, or through a closed harvest system under positive pressure. The bulk harvested virus is frozen and stored at a temperature from about −40° C. to about −70° C.

Aliquots are obtained for quality control measurements, as required. Samples of each bulk harvest are tested in thioglycolate and soybean casein digest media, which is incubated at about 36° C. and 20° C., respectively, for 14 days at each temperature. This seed virus is used to spawn subsequent cultures if testing indicates a titer of at least about 10$^5$ TCID$_{50}$/ml by CPE. Unsatisfactory material is sterilized with 5% sodium hypochlorite for 24 hours or autoclaved.

Steps P20 includes stabilizing and lyophilizing the bulk frozen virus obtained in step P18. The bulk frozen virus is thawed, and preferably mixed with a pharmacologically compatible stabilizer, such as a conventional sucrose gelatin stabilizer, in a ratio of about three parts of thawed Master Seed Culture to about one part of stabilizer. Physiological saline may be added to adjust the final virus concentration.

The mixture is then divided into subvolumes of doses of about 0.28 ml of fluid each, with each dose including about 0.20 ml of PRRS culture per dose at a minimum titer of 10$^{4.9}$ TCID$_{50}$ per dose. It is here noted that the preferred amount of stabilized production culture that results from steps P16, P18, and P20 will be sufficient to yield between 150,000 and 500,000 stabilized doses. By way of example, 25 doses would comprise approximately 7.0 ml subvolume. These subvolumes are plug frozen, preferably, in liquid nitrogen. The drying chamber is held under vacuum while the temperature is raised to a maximum of about 30° C., and the subvolume is held for a maximum of 18 hours to sublime moisture in the sample.

Step P22 includes continuous monitoring of the vaccine product that results from step P20. A container of final samples or a serial of a single batch of PRRS vaccine is spot-checked to assure that moisture contents fall below 5%. Serials with moisture contents greater than 4% or less than 1% will be tested for potency at six month intervals. As a safety measure, Guinea pigs are injected with the weight equivalent of 10 doses of vaccine, and observed over 21 days for untoward signs of clinical reaction.

The VR-2332 virus was also cold-adapted in parallel with the attenuation described in Example 1. This was done in order to develop a vaccine strain that prevented shedding of the virus by infected animals. Such cold adaptation was carried out by successive passages at a temperature of 31–35° C. The resultant strains would also stimulate an immune response.

What is claimed is:

1. A vaccine composition comprising live porcine reproductive and respiratory syndrome (PRRS) virus in a modified form and mixed with a pharmacologically compatible carrier agent, said modified virus comprising ATCC-VR2332 virus passaged at least 70 times in cell culture such that when the modified virus is administered to a swine or other mammal prone to PRRS, it fails to cause clinical signs of PRRS disease but is capable of inducing an immune response that immunizes the mammal against pathogenic forms of PRRS.

2. The composition as set forth in claim 1, said virus comprising ATCC-VR2495.

3. The composition as set forth in claim 1, said carrier agent comprising sucrose gelatin stabilizer.

4. A method of immunizing swine against porcine reproductive and respiratory syndrome (PRRS), said method comprising the step of administering to swine a vaccine composition including a live porcine reproductive and respiratory syndrome virus mixed with a pharmacologically compatible carrier agent, said virus comprising ATCC-VR2332 virus passaged at least 70 times in cell culture to modify the virus such that when the modified virus is administered to a swine or other mammal prone to PRRS, it fails to cause clinical signs of PRRS disease but is capable of inducing an immune response that immunizes the mammal against pathogenic forms of PRRS.

5. A method of producing commercial quantities of PRRS vaccine, comprising the steps of:

preparing a production culture of a modified form of the ATCC-VR2332 virus, including the steps of passaging ATCC-VR2332 virus at least 70 times in cell culture to modify the virus such that when the modified virus is administered to a swine or other mammal prone to PRRS, it fails to cause clinical signs of PRRS disease but is capable of inducing an immune response that immunizes the mammal against pathogenic forms of PRRS, and generating a production culture from the modified ATCC-VR2332 virus;

harvesting the production virus culture;

adding a stabilizing agent to the production virus culture; and lyophilizing the production virus culture.

6. The method as set forth in claim 5, wherein the step of preparing includes infecting a simian cell line with said virus, and incubating the resultant culture at a temperature of from about 35° C. to about 37° C.

7. The method as set forth in claim 5, wherein the step of harvesting includes freezing the virus culture.

8. The method as set forth in claim 5, wherein the step of adding includes mixing about one part of sucrose gelatin stabilizer with about three parts of the virus culture.

9. The method as set forth in claim 5, wherein the step of lyophilizing includes subliming moisture from a frozen sample of the virus culture.

10. The method as set forth in claim 5, wherein said culture includes a serial volume of from 150,000 to 500,000 doses of 0.28 ml per dose.

11. The method as set forth in claim 10 further including subdividing the serial volume prior to the step of lyophilizing.

12. The method as set forth in claim 5, wherein said substantially avirulent virus is ATCC 2495 virus.

13. A vaccine produced according to the method of claim 5.

14. The method of claim 4, said virus being passaged 75 times.

15. The composition of claim 1, said virus being passaged 75 times.

16. The method of claim 5, said virus being passaged 75 times.

* * * * *